(12) United States Patent
Wang et al.

(10) Patent No.: US 7,169,578 B2
(45) Date of Patent: Jan. 30, 2007

(54) CELL ISOLATION AND SCREENING DEVICE AND METHOD OF USING SAME

(75) Inventors: Evelyn Wang, Haddonfield, NJ (US); Rocco Casagrande, Newton, MA (US); Amar Kendale, Somerville, MA (US); Enoch Kim, Boston, MA (US); Emanuele Ostuni, Watertown, MA (US); Olivier Schueller, Somerville, MA (US)

(73) Assignee: Surface Logix, Inc., Brighton, MA (US)

(*) Notice: Subject to any disclaimer, the term of this patent is extended or adjusted under 35 U.S.C. 154(b) by 352 days.

(21) Appl. No.: 10/206,341

(22) Filed: Jul. 29, 2002

(65) Prior Publication Data

US 2003/0032071 A1 Feb. 13, 2003

Related U.S. Application Data (63) Continuation-in-part of application No. 10/084,063, filed on Feb. 28, 2002.

(60) Provisional application No. 60/334,593, filed on Dec. 3, 2001, provisional application No. 60/307,843, filed on Jul. 27, 2001.

(51) Int. Cl.
*C12Q 1/24* (2006.01)

(52) U.S. Cl. ............... 435/30; 435/29; 435/4; 435/325; 435/326; 435/288.4; 435/305.4; 435/70.2

(58) Field of Classification Search ............ 435/326, 435/383, 287.2, 287.6, 288.4, 305.2, 308.1, 435/70.21; 209/17

See application file for complete search history.

(56) References Cited

U.S. PATENT DOCUMENTS 4,230,685 A  10/1980  Senyei et al.
4,408,625 A  10/1983  Kuhl (Continued)

FOREIGN PATENT DOCUMENTS

EP    0 390 634 B1    5/1995

(Continued)

OTHER PUBLICATIONS

Yokoyama, "Production of Monoclonal Antibodies" Current Protocols in Cell Biology, 1999, 16.1.1-16.1.17.*

(Continued)

*Primary Examiner*—Leon B. Lankford, Jr.
*Assistant Examiner*—Allison M. Ford
(74) *Attorney, Agent, or Firm*—Kenyon & Kenyon LLP (57) ABSTRACT

The present invention provides methods and devices for screening a single cell or a small group of cells for a desired biological activity. In particular, the present invention provides for delivering cell(s) to a plurality of cell isolation regions of a cell isolation device, transferring the cell(s) to a plurality of wells of a cell expansion device and detecting the potential desired biological activity of the cell(s). Each of the cell isolation regions comprise a bioaffinity region capable of binding a single cell or a small group of cell(s). This binding of cell(s) may be accomplished through the use of bioaffinity ligands immobilized in the bioaffinity regions of the cell isolation regions. Preferably, the wells of the cell expansion device encompass a cavity that provides sufficient volume for cell proliferation.

17 Claims, 6 Drawing Sheets

U.S. PATENT DOCUMENTS

| | | | |
|---|---|---|---|
| 4,508,625 A | | 4/1985 | Graham |
| 4,582,622 A | | 4/1986 | Ikeda et al. |
| 4,591,570 A | | 5/1986 | Chang |
| 4,672,040 A | | 6/1987 | Josephson |
| 4,729,949 A | * | 3/1988 | Weinreb et al. ............... 435/30 |
| 4,748,124 A | | 5/1988 | Vogler |
| 4,777,145 A | | 10/1988 | Luotola et al. |
| 4,910,148 A | | 3/1990 | Sorensen et al. |
| 4,988,618 A | | 1/1991 | Li et al. |
| 4,992,377 A | | 2/1991 | Saxholm |
| 5,186,827 A | | 2/1993 | Liberti et al. |
| 5,200,084 A | | 4/1993 | Liberti et al. |
| 5,202,227 A | | 4/1993 | Matsuda et al. |
| 5,278,063 A | | 1/1994 | Hubbell et al. |
| 5,330,911 A | | 7/1994 | Hubbell et al. |
| 5,395,498 A | | 3/1995 | Gombinsky et al. |
| 5,427,663 A | | 6/1995 | Austin et al. |
| 5,466,574 A | | 11/1995 | Liberti et al. |
| 5,476,796 A | | 12/1995 | Takahashi et al. |
| 5,486,457 A | | 1/1996 | Butler et al. |
| 5,498,392 A | | 3/1996 | Wilding et al. |
| 5,498,550 A | | 3/1996 | Fujiwara et al. |
| 5,508,164 A | | 4/1996 | Kausch et al. |
| 5,514,340 A | | 5/1996 | Landsdorp et al. |
| 5,567,326 A | | 10/1996 | Ekenberg et al. |
| 5,573,942 A | | 11/1996 | Miyamoto |
| 5,591,627 A | | 1/1997 | Miyamoto |
| 5,593,838 A | | 1/1997 | Zanzucchi et al. |
| 5,602,028 A | | 2/1997 | Minchinton |
| 5,602,042 A | | 2/1997 | Farber |
| 5,603,351 A | * | 2/1997 | Cherukuri et al. .......... 137/597 |
| 5,612,188 A | | 3/1997 | Shuler et al. |
| 5,646,001 A | | 7/1997 | Terstappen et al. |
| 5,660,990 A | | 8/1997 | Rao et al. |
| 5,665,582 A | | 9/1997 | Kausch et al. |
| 5,681,484 A | | 10/1997 | Zanzucchi et al. |
| 5,755,942 A | | 5/1998 | Zanzucchi et al. |
| 5,759,793 A | | 6/1998 | Schwartz et al. |
| 5,763,203 A | | 6/1998 | Ugelstad et al. |
| 5,776,748 A | | 7/1998 | Singhvi et al. |
| 5,795,470 A | | 8/1998 | Wang et al. |
| 5,812,419 A | | 9/1998 | Chupp et al. |
| 5,858,804 A | | 1/1999 | Zanzucchi et al. |
| 5,876,593 A | | 3/1999 | Liberti et al. |
| 5,912,177 A | | 6/1999 | Turner et al. |
| 5,922,284 A | | 7/1999 | Kinoshita et al. |
| 5,928,880 A | | 7/1999 | Wilding et al. |
| 5,968,820 A | | 10/1999 | Zborowski et al. |
| 5,972,721 A | | 10/1999 | Bruno et al. |
| 5,989,835 A | | 11/1999 | Dunlay et al. |
| 5,993,665 A | | 11/1999 | Terstappen et al. |
| 5,993,740 A | | 11/1999 | Niiyama et al. |
| 5,998,160 A | | 12/1999 | Berens |
| 5,998,224 A | | 12/1999 | Rohr et al. |
| 6,008,010 A | | 12/1999 | Greenberger et al. |
| 6,013,188 A | | 1/2000 | Terstappen et al. |
| 6,013,532 A | | 1/2000 | Liberti et al. |
| 6,027,945 A | | 2/2000 | Smith et al. |
| 6,039,897 A | | 3/2000 | Lochhead et al. |
| 6,083,761 A | * | 7/2000 | Kedar et al. ................ 436/178 |
| 6,090,251 A | | 7/2000 | Sundberg et al. |
| 6,110,380 A | | 8/2000 | Barbera-Guillem |
| 6,126,835 A | | 10/2000 | Barbera-Guillem et al. |
| 6,133,043 A | | 10/2000 | Talley et al. |
| 6,136,182 A | | 10/2000 | Dolan et al. |
| 6,140,045 A | | 10/2000 | Wohlstadter et al. |
| 6,143,247 A | | 11/2000 | Sheppard, Jr. et al. |
| 6,180,239 B1 | | 1/2001 | Whitesides et al. |
| 6,180,418 B1 | | 1/2001 | Lee |
| 6,184,043 B1 | | 2/2001 | Fodstad et al. |
| 6,187,214 B1 | | 2/2001 | Gañán-Calvo |
| 6,221,663 B1 | | 4/2001 | Bhatia et al. |
| 6,235,541 B1 | | 5/2001 | Brizzolara |
| 6,238,538 B1 | | 5/2001 | Parce et al. |
| 6,258,607 B1 | | 7/2001 | Saito et al. |
| 6,558,904 B2 | | 5/2003 | Ermantraut et al. |
| 2002/0012953 A1 | | 1/2002 | Jauho et al. |
| 2002/0022276 A1 | | 2/2002 | Zhou et al. |

FOREIGN PATENT DOCUMENTS

| | | |
|---|---|---|
| JP | 63-116175 | 5/1988 |
| WO | WO 92 08133 | 5/1992 |
| WO | WO 94 11078 | 5/1994 |
| WO | WO 97 28490 | 8/1997 |
| WO | WO 99 42832 | 8/1999 |
| WO | WO 00 43783 | 7/2000 |
| WO | WO 00 54882 | 9/2000 |
| WO | WO 00 60356 | 10/2000 |
| WO | WO 01 51668 | 7/2001 |

OTHER PUBLICATIONS

Hornbeck et al, "Enzyme-Linked Immunosorbet Assays (ELISA)," Current Protocols in Molecular Biology, 1991, 11.2.1-11.2.22.*

Castelino J., *"Magnetic Activated Cell Sorting using Microfabricated Arrays"*, Biomedical Physics (1999). Session Z13. 001 (abstract).

Fishman D. et al., *"Biological Assays in Microfabricated Structures"*, SPIE (1999) 3603:192-197.

Folch A. et al., *"Microengineering of Cellular Interactions"*, Annu. Rev. Biomed. Eng. (2000) 2:227-256.

Beebe et al., *"Microfluidic tectonics: A comprehensive construction platform for microfluidic systems"*, PNAS. 97(25):13488-13493 (2000).

Bhatia et al., *"Selective Adhesion of Hepatocytes on Patterned Surfaces"*, Annals New York Academy of Sciences. 745:187-209(1994).

Blawas et al., *"Protein Patterning"*, Biomaterials. 19:595-609(1998).

Boone et al., *"Plastic Advances Microfluidic Devices"* Analytical Chemistry. 74(3):78A-86A (2002).

Britland et al., *"Micropatterning Proteins and Synthetic Peptides on Solid Supports: A Novel Application for Microelectronics Fabrication Technology"*, Biotechnol. Prog . . . 8:155-160 (1992).

Chen et al., *"Using Self-Assembled Monolayers to Pattern ECM Proteins and Cells on Substrates"*, Methods in Molecular Biology Extracellular. Matrix Protocols. 139:209-218.

Chiu et al., *"Patterned deposition of cells and proteins onto surfaces by using three-dimensional microfluidic systems"*, PNAS. 97(6):2408-2413 (2000).

Dasgupta et al., *"Visualizing thin-layer. 2-D flow and chemical interaction can be done simply and cheaply"*, Analytical Chemistry. 74(7):209A-213A (2002).

Delamarche et al., *"Patterned Delivery of Immunoglobulins to Surfaces Using Microfluidic Networks"*, Science. 276:779-781 (1997).

Delamarche et al., *"Microfluidic Networks for Chemical Patterning of Substrates: Design and Application to Bioassays"*, J. Am. Chem. Soc., 120:500-508 (1998).

Hodneland et al., *"Selective immobilization of proteins to self-assembled manolayers presenting active site-directed capture ligands"*, PNAS. 99(8):5048-5052 (2002).

Jung et al., *Topographical and Physicochemical Modification of Material Surface to Enable Patterning of Living Cells*, Critical Reviews in Biotechnology. 21(2):111-154 (2001).

Love et al., *"Fabrication of Three-Dimensional Microfluidic Systems by Soft Lithography"*, MRS Bulletin. 26 (7):523-527 (2001).

Quake et al., *"From Micro-to-Nanofabrication with Soft Materials"*, Science. 290(5496):1536-1540 (2000).

Safarik et al., *"Use of magnetic techniques for the isolation of cells"*, Journal of Chromatography B. 722:33-53 (1999).

Saleemuddin. *"Bioaffinity Based Immobilization of Enzymes"*, Advances in Biochemical Engineering Biotechnology. 64: 203-226 (1999).

Yang et al., "Il-18-stimulated GADD45β required in cytokine-induced, but not TCR-induced. IFN-γ production", *Abstracts 2.1-537.42 Part 1—Experimental Biology 2001. Orlando Florida, Mar. 31-Apr. 4, 2001*, FASEB Journal. Abstract 537.40.

\* cited by examiner

CELL ISOLATION AND SCREENING DEVICE AND METHOD OF USING SAME

CROSS-REFERENCE TO RELATED APPLICATIONS

This application is a continuation-in-part application of U.S. application Ser. No. 10/084,063, filed Feb. 28, 2002 and claims the benefit of Provisional U.S. Application Ser. No. 60/334,593 filed Dec. 3, 2001, and Provisional U.S. Applicaton Ser. No. 60/307,843 filed Jul. 27, 2001, all of which herein incorporated by reference in their entirety.

FIELD OF THE INVENTION

The present invention relates to devices and methods that are useful for isolating and screening cells for a desired biological activity. In particular, the present invention relates to devices and methods that are useful in isolating and screening hybridoma cells for specific antibody production.

BACKGROUND OF THE INVENTION

One of the major challenges for performing cell based screening is the isolation of small populations of cells in a manner that allows for subsequent screening procedures. Traditional devices and methods of isolating cells do not adequately provide for the isolation of small populations of cells without performing steps that potentially modify cellular function or activity. Isolation of cells is not only important in screening, but also in processes that involve the monitoring, measuring, and/or use of the output of cellular activity or function (e.g. antibody production) for small populations of cells.

For example, with respect to antibody production, one of the approaches used to produce antibodies is to manufacture hybridomas. These are cells created by the fusion of antibody-secreting B-cells and myeloma cells. This method is variable with respect to almost all stages of the process including the duration of screening and required needs for cell growth and proliferation. Much of the variability can be attributed to the immunogen and immune response mounted by the immunized animal. Moreover this process is time consuming and labor intensive.

In general, once the fusion is performed and the cells are plated, there are several issues that have to be addressed. First, the cells will grow at different rates, thus the point at which one must perform the assay for antibody production to assess positive pools of cells can vary and may require more than one assay point on the same pool of cells. During this process, the rapidly growing cells need to be passaged in order to promote viability and to prevent loss of potentially positive clones. The next step is to perform limiting dilution with the goal of achieving clonal populations. Successive rounds of this process may be required to achieve clonal or near clonal populations.

The value of specific monoclonal antibodies as useful tools for diagnostics and immuno-therapies has meant that investigators have had no alternative but to tolerate long production periods and high development costs. Rapid and efficient ways of screening hybridoma cell lines for antibody production are not presently available. Therefore, there is a need for methods and devices to accelerate monoclonal antibody production for experimental, diagnostic and therapeutic applications. The devices and methods disclosed herein dramatically shorten the period for monoclonal antibody production from a period of weeks to a period of days. The invention provides a multicomponent device that also has application for other cell types requiring the isolation of a small population of cells and requiring the subsequent clonal expansion of this population of cells.

SUMMARY OF THE INVENTION

The present invention relates to devices and methods for screening a cell or small group of cells for a desired biological activity comprising a cell delivery step, a cell isolation device and a corresponding cell isolation step, a cell expansion device and a corresponding cell expansion step, and a detection device and a corresponding detection step.

In particular, the present invention provides a method of screening cells for a desired biological activity comprising providing a cell isolation device defining a plurality of cell isolation regions, each cell isolation region being sized for isolating about one to about five cells therein, each cell isolation region encompassing a bioaffinity region, the cell isolation regions further defining a predetermined pitch with respect to one another. The method further comprises delivering the about one cell to about five cells to each of the cell isolation regions. The method moreover comprises providing a cell expansion device defining a plurality of wells corresponding to respective ones of the plurality of cell isolation regions and defining a predetermined pitch that matches the predetermined pitch of the cell isolation regions. The method additionally comprises transferring the about one to about five cells from the cell isolation regions to the wells and allowing about one cell to about five cells to proliferate and exhibit a desired biological activity. The method also comprises assaying the biological activity the about one to about five cells.

The present invention also provides a kit for screening cells for a desired biological activity, the kit comprising a cell isolation device defining a plurality of cell isolation regions, each of the cell isolation regions being sized to isolate about one cell to about five cells therein, and each encompassing a bioaffinity region, the cell isolation device further defining a predetermined pitch with respect to one another. The kit also comprises a cell expansion device defining a plurality of wells corresponding to respective ones of the plurality of cell isolation regions.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE INVENTION

The present invention relates to methods and devices for isolating a small population of cells and for screening a larger population of proliferated cells for biological activity with a minimal amount of manipulation of the cells. Although the present invention contemplates the screening of all types of cells for the detection of any desired biological activity, for purposes of illustration, the methods and devices described herein are occasionally described in the context of isolating and screening hybridoma cells for specific antibody production. The present invention is not in any way limited to this application and may be used to isolate any types of cells, including all cell lines that secrete substances that can be isolated. Such cell lines include cell lines that secrete or express, for example, antibodies, proteins, carbohydrates, enzymes, peptides, hormones, and receptors. Other cells include, for example, B-cells; T-cells; non-adherent cells like epothelial cells and endothelial cells; oncogenic cell line; genetically engineered cells; and activated cells. Moreover, the present invention may be used to screen for a variety of biological activities including, but not limited to, the expression of surface receptor proteins, enzyme production, and peptide production. Furthermore, the present invention may be used to screen a variety of test agents to determine the effect of the test agents on the desired biological activity. Other types of cells desired to be isolated and screened, other types of biological activity desired to be detected, and specific test agents to be screened will be readily appreciated by one of skill in the art.

In general, the present invention relates to a method and accompanying device for isolating and screening cells including a cell delivery step, a cell isolation step utilizing a cell isolation device, a cell expansion step utilizing a cell expansion device, and a detection step utilizing a detection device. In general, cells are delivered to cell isolation regions of the cell isolation device. By "cell isolation region" is meant any area capable of attracting, trapping, securing and/or binding a single cell or a small population of cells. Cell are then transferred to wells of a cell expansion device. By "well" is meant a cavity that is capable of retaining cells therein. Cells are then transferred from the cell expansion device to the detection device where biological activity is detected, or, in the alternative, the detection device is brought into contact with the cell expansion device.

With respect to particular details of the methods and devices according to the present invention, in the cell delivery step, cells may be delivered to the cell isolation regions of the cell isolation device (described in more detail below) by any means known in the art. For example, cells may be delivered by directly pipetting cells into or on the cell isolation regions of the cell isolation device either manually or by robotic liquid handling systems; bulk delivering the cells in fluid to the cell isolation device and removing the excess by pipetting so as to leave only cells in or on the cell isolation regions; or by utilizing a delivery device with microfluidic channels to deliver the cells into or on the cell isolation regions.

Figure 1:
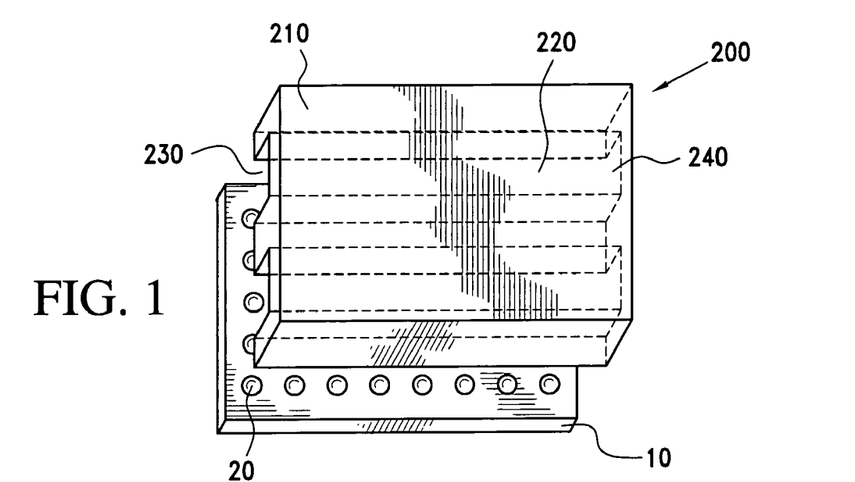
FIG. 1 is a top perspective view of an embodiment of a cell delivery device and an embodiment of a cell isolation device according to the present invention.
Figure 3:
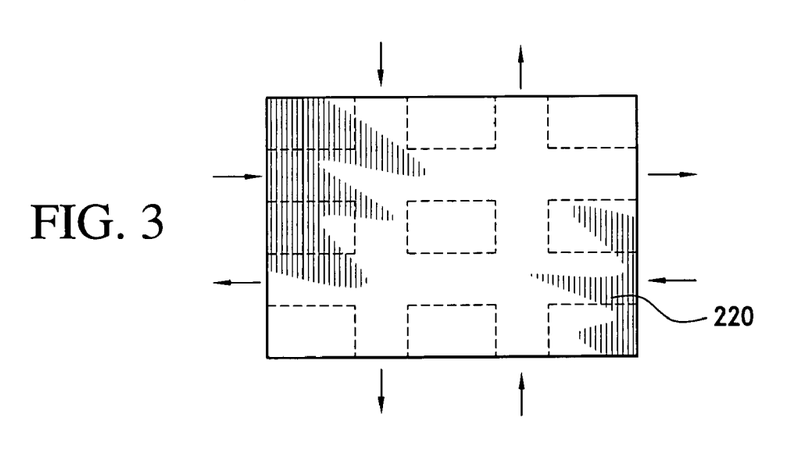
FIG. 3 is a schematic view of the channel pathways of an embodiment of the cell delivery device according to the present invention.

FIG. 1 illustrates an example of a microfluidic delivery device 200 with microfluidic channels 220 to deliver the cells into or on cell isolation regions 20 of cell isolation device 10. "Microfluidic delivery device," as used herein, refers to a system or device having fluidic conduits, such as channels, that are typically fabricated at the micron to submicron scale. Generally, the fluidic conduits have at least one cross-sectional dimension in the range of from about 0.1 μm to about 500 μm. As seen in FIG. 1, the microfluidic device 200 generally comprises a housing 210 defining a plurality of channels 220. Each channel includes an entrance port 230 at one end and an exit port 240 at another end. Although FIG. 1 depicts only two channels, microfluidic device 200 can include more than two channels 220 as seen in FIG. 3 (wherein dashed lines indicate channel paths and arrows indicate potential flow in multiple directions through each channel). The diameter of channels 220 should be large enough to prevent clogging of channels 220, preferably being about three times the diameter of the cell. A 100 μm×100 μm channel is the preferred size yet alternate sizes may include, but are not limited to, 60 μm×100 μm or 30 μm×100 μm. Although a microfluidic device for use in the present invention is described briefly below, methods of employing microfluidics for cell delivery are well-known in the art and are described, for example, in Love, et al., MRS BULLETIN, pp. 523–527 (July 2001) "Fabrication of Three-Dimensional Microfluidic Systems by Soft Lithography," Delamarche et al,: JOURNAL OF AMERICAN CHEMICAL SOCIETY, Vol. 120, pp. 500–508 (1998), Delamarche et al,: SCIENCE, Vol. 276, pp.779–781 (May 1997), Quake et al., SCIENCE, Vol. 290, pp. 1536–1540 (Nov. 24, 2000), all of which are hereby incorporated by reference.

Figure 2:
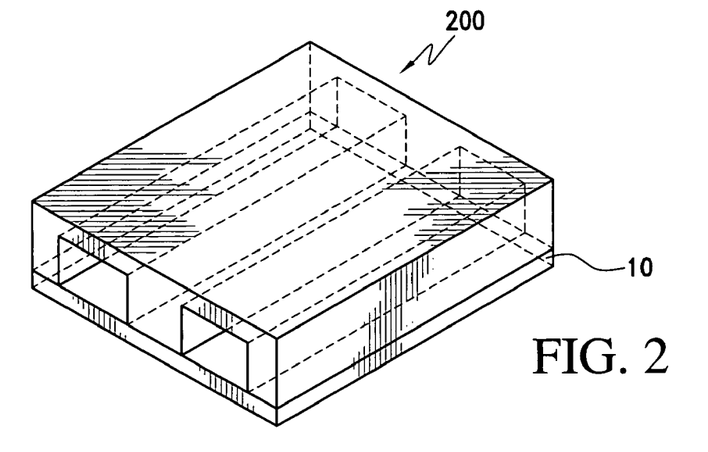
FIG. 2 is a perspective view of an embodiment of a cell delivery device according to the present invention in contact with an embodiment of a cell isolation device according to the present invention.

With respect to the use of microfluidic device 200 according to the present invention, as seen in FIG. 2, microfluidic device 200 is contacted with the top surface of cell isolation device 10 to provide a substantially fluid-tight seal. Cell are delivered to the cell isolation regions by flowing medium containing the cells desired to be isolated through channels 220 over cell isolation regions 20. The flowing of the medium containing the cells through channels 220 of microfluidic device 200 may be carried out by a number of mechanisms, including, for example, pressure based flow, electrokinetic flow, or mechanisms that utilize a hybrid of the two. Microfluidic device 200 may also include integrated microfluidic structures, such as micropumps and microvalves, or external elements, e.g., pumps and switching valves, for the pumping and direction of the medium through device 200. Medium transport and direction may also be accomplished through electroosmosis or electrokinesis. The selection and details of the above mechanisms would be well within the knowledge of a person skilled in the art.

In some embodiments of the present invention, preferably the flow of the cell containing medium into the cell isolation regions is constant, or continuous. Typically, a known and/or constant flow rate is useful, for example, when attempting to establish precise control over the delivery of cells to cell isolation regions 20. Furthermore, constant flow facilitates feeding of cells and high throughput screening.

In one embodiment of the method of delivering cells to cell isolation device 10 according to the present invention, microfluidic device 200 is used to deliver about fifty to about hundred cells to each cell isolation region 20. In another embodiment, microfluidic device 200 is used to deliver about twenty-five to about fifty cells to each cell isolation region 20. In yet another embodiment, microfluidic device 200 is used to delivery about ten to about twenty-five cells to each cell isolation region 20. In another embodiment, microfluidic device 200 is used to delivery about five to about ten cells to each cell isolation region 20. In still another embodiment, microfluidic device is used to delivery about one to about five cells to each cell isolation region 20. In a preferred embodiment, microfluidic device is used to deliver a single cell to each cell isolation region 20. Typically, about 90% of each of the cell isolation regions 20 of the cell isolation device 10 are filled when the flow rate is adjusted or regulated. The flow rate by which the cell containing medium is delivered to the cell isolation regions 20 can be adjusted by known methods. A person of skill in the art would know how to adjust the flow rate of a microfluidic device to achieve a desired cell distribution per cell isolation region 20.

Microfluidic device 200 may be fabricated from materials that are compatible with the conditions present in the particular experiment of interest. Such conditions include, but are not limited to, pH, temperature, ionic concentration, pressure, and application of electrical fields. The materials of device 200 may also be chosen for their inertness to components of the experiment to be carried out in the device. Such materials include, but are not limited to, glass, silicon, fused silica, metal films, polymeric substrates, such as polystyrene, poly(methylacrylate), polydimethylsiloxane (PDMS) and polycarbonate, depending on the intended application.

Figures 4, 5, 6, 7, 8, 9A, 9B:
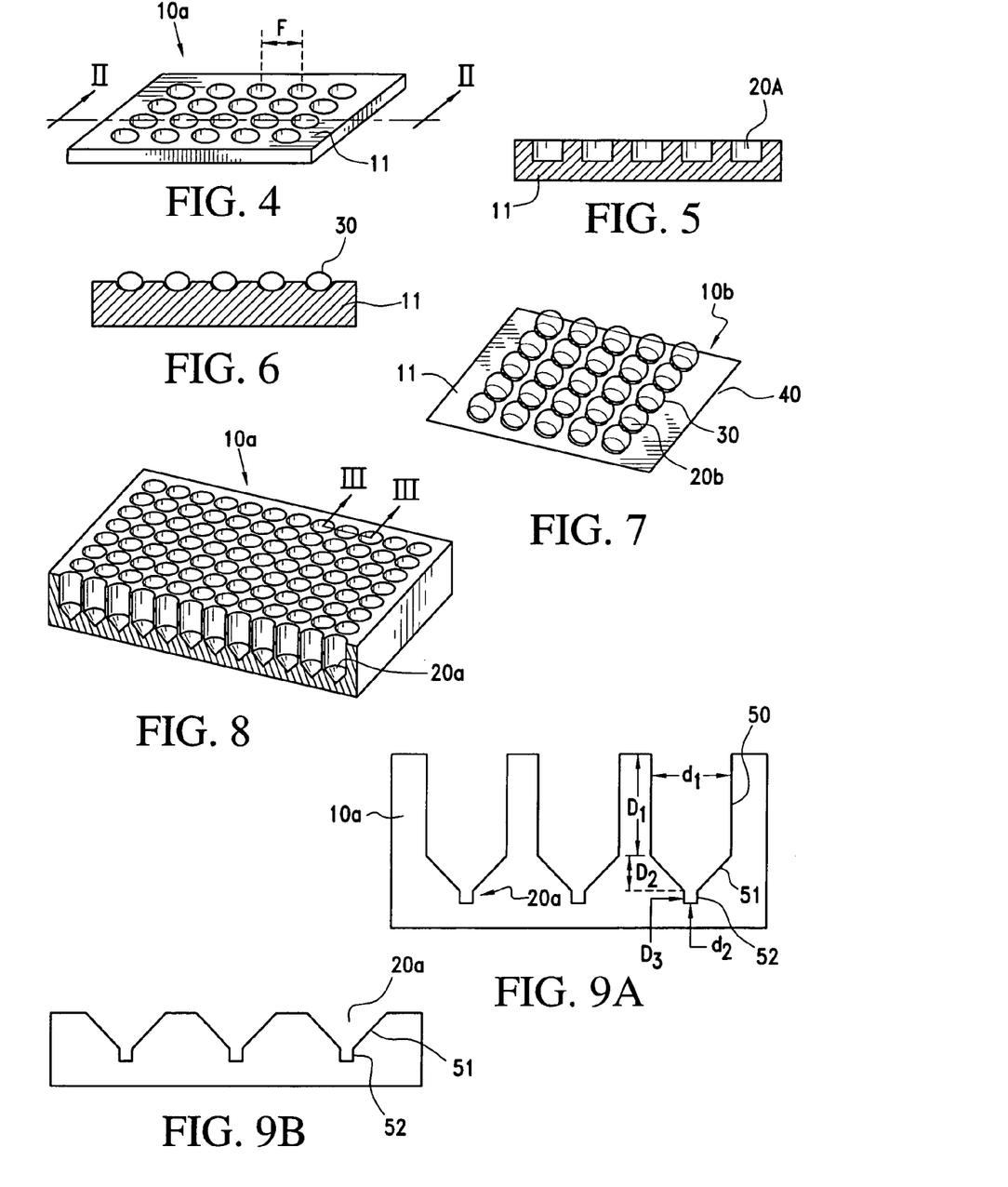
FIG. 4 is an oblique perspective view of an embodiment of a cell isolation device according to the present invention.
FIG. 5 is a cross-sectional view of the device of FIG. 4 along lines II—II.
FIG. 6 is a cross-sectional view of the device of FIG. 4.
FIG. 7 is an oblique perspective view of an alternative embodiment of a cell isolation device according to the present invention.
FIG. 8 is a partially cut-away perspective view of an embodiment of a cell isolation device according to the present invention.
FIG. 9A is a cross-sectional view of the cell isolation device of FIG. 8 along lines III—III showing an embodiment of the cell isolation regions of the cell isolation device.
FIG. 9B is a view similar to FIG. 8 showing an alternative embodiment of the cell isolation regions of the cell isolation device.

Notwithstanding the method of delivery, according to embodiments of the present invention, cells are ultimately delivered to cell isolation device 10 where cells are isolated. As illustrated in FIG. 4 and FIG. 7, cell isolation device 10(a/b) utilized in the cell isolation step generally includes a plurality of cell isolation regions 20(a/b) for receiving cells therein.

FIGS. 4–6 show one embodiment of a cell isolation device according to the present invention, where the cell isolation device 10a generally includes a housing 11 defining a plurality of cell isolation regions 20a into which cells 30 may be delivered. Cell isolation region 20a presents a recess sized to isolate a single cell 30 or a small group of cells 30. In one embodiment, cell isolation region 20a is sized to isolate about fifty to about hundred cells. In another embodiment, cell isolation region 20a is sized to isolate about twenty-five to about fifty cells. In yet another embodiment, cell isolation region 20a is sized to isolate about ten to about twenty-five cells. In another embodiment, cell isolation region 20a is sized to isolate about five to about ten cells. In still another embodiment, cell isolation region 20a is sized to isolate about one to about five cells. In a preferred embodiment, cell isolation region 20a is sized to isolate a single cell.

In another embodiment of the cell isolation device, as seen in FIG. 7, cell isolation device 10b is generally defined by a surface 40 defining a plurality of cell isolation regions 20b upon which cells 30 may be delivered. Preferably, surface 40 is planar. In the embodiment depicted in FIG. 7, cell isolation region 20b, corresponds to a discrete area of surface 40 that has the ability to attract, trap, secure and/or bind a cell 30 or a small group of cells 30 thereon with respect to the non-attractive surrounding surface 40 (such discrete area referred to herein as a "bioaffinity region"). This ability to secure cells 30 to the bioaffinity region may be accomplished through the use of "bioaffinity ligands" as disclosed in more detail herein. With respect to the size of cell isolation region 20b, in one embodiment, cell isolation region 20b is sized to isolate about fifty to about hundred cells. In another embodiment, cell isolation region 20b is sized to isolate about twenty-five to about fifty cells. In yet another embodiment, cell isolation region 20b is sized to isolate about ten to about twenty-five cells. In another embodiment, cell isolation region 20b is sized to isolate about five to about ten cells. In still another embodiment, cell isolation region 20b is sized to isolate about one to about five cells. In a preferred embodiment, cell isolation region 20b is sized to isolate a single cell.

Notwithstanding the type of cell isolation region 20 utilized, preferably adjacent cell isolation regions 20 are disposed relative to one another to define a predetermine pitch. More, preferably, the cell isolation regions 20 are disposed relative to one another to match a pitch P of an industry standard microtiter plate such as, for example, a 24-, 96-, 384-, 768-, or a 1536-well microtiter plate. The term "pitch" P as used herein in reference to the cell isolation device, the cell expansion device, and the cell detection device, refers to the distance between respective vertical centerlines between adjacent cell isolation regions 20 in the test orientation of the particular device being utilized. By "test orientation" of the device is meant to refer to a spatial orientation of the cell isolation device of the particular device being utilized during its respective step. For example, the test orientation of the cell isolation device 10 is the orientation of the device when cells are isolated in their respective cell isolation regions 20. The test orientation of the cell expansion device is the orientation of the cell expansion device when cells are allowed to proliferate in their respective wells. It is also noted that in the context of the present invention, "top," "bottom," and "lateral" are defined relative to the test orientation of the cell isolation device.

Although the present invention contemplates both the isolation of a single cell 30 and small groups of cells 30, in certain embodiments it may be preferable to isolate a single cell 30. Examples of such embodiments include the embodiments of FIGS. 9A and 9B, which respectively show alternative embodiments of cell isolation region 20a. Referring to FIGS. 9A and 9B, the shown embodiments of cell isolation device 10a, show cell isolation region 20a that is defined by a microwell portion 52. The microwell portion 52 may adjoin accessory delivery portions including a conical portion 51. Additionally, in the embodiments of FIGS. 8 and 9A, another accessory delivery portion, top cylindrical portion 50, adjoins conical portion 51, which in turn, adjoins the bottom microwell portion 52. The dimensions of the accessory delivery portions 51 and 52 and the cell isolation region, microwell portion 52, may include any dimensions that allow for cells to be added to the cell isolation regions 20a en masse yet permit only a single cell to settle into microwell portion 52 of cell isolation region 20a. Preferably, as depicted in FIG. 9B, the cylindrical portion 50 (in embodiments including portion 50) has a diameter $d_1$ of about 2 millimeters (mm) and a depth $D_1$ of about 3 mm; the conical portion 51 has a depth $D_2$ of about 1 mm; and the microwell portion 52 has a diameter $d_3$ of about 10 microns (μm) to about 50 μm and a depth $D_3$ of about 10 μm to about 50 μm. In a preferred embodiment, the diameter $d_3$ of microwell portion 52 is about 20 μm and the depth $D_3$ of microwell portion is about 20 μm. The cell isolation regions 20a may also be disposed relative to one another to match a pitch of a standard microtiter plate such as, for example, a 24-, 96-, 384-, 768-, or a 1536-well microtiter plate.

Figures 10A, 10B, 10C:
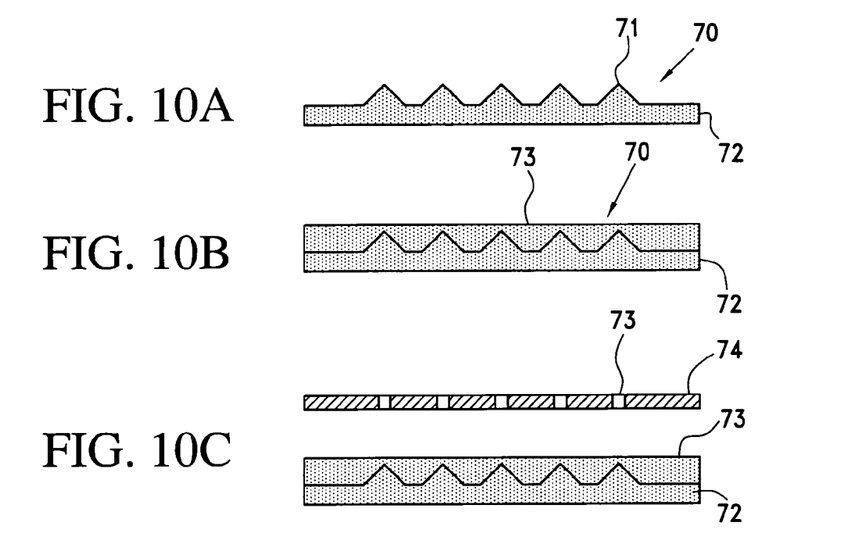
FIGS. 10A–E shows respective stages of a method of fabricating an embodiment of the cell isolation device according to the present invention.
Figure 10D:
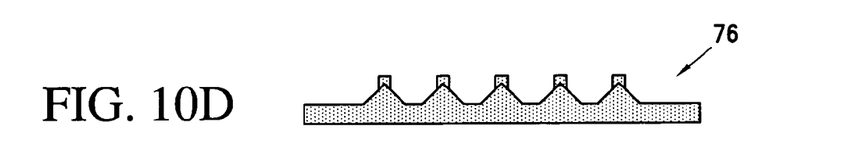
Figure 10E:
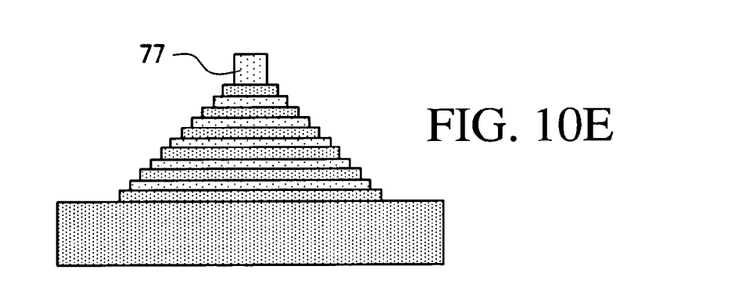

The present invention contemplates several methods of fabricating cell isolation device 10a wherein cell isolation region 20a of device 10a is defined a microwell portion 52 and accessory delivery portions such as conical portion 51 and optionally cylindrical portion 50. Referring to FIGS. 10(A–E), various stages of an embodiment of a fabrication method according to the present invention are shown. According to the shown embodiment of the fabrication method, device 10a may be fabricated by standard photolithographic procedures. According to this procedure, a substrate 70, as seen in FIG. 10A, defining a plurality of conical elements 71 thereon extending from a base 72 is fabricated via standard machining methods. The dimensions of each conical element 71 corresponds to the dimensions of a corresponding conical portion 51 and may be machined directly into base 72 or attached to base 72 by mechanical means, such as by press-fitting, or chemical means, such as by adhesive bonds. Alternatively, conical elements 71 may be fabricated by a multi-level photolithography technique resulting in a quasi-conical topology of sequentially decreasing layers of photoresist as seen in FIG. 10E. The final layer 77 of photoresist corresponds to the dimensions of microwell portion 52. In a preferred embodiment and as illustrated in FIGS. 10A–E and 11, conical elements 71 are disposed relative to one another to match a pitch of a standard microtiter plate. In an alternative embodiment (not shown), substrate 70 is further defined by a plurality of cylindrical elements. With respect to a singly representative cylindrical element, the cylindrical element is positioned between base 72 and a conical element 71. The dimensions of the cylindrical elements correspond to the dimensions of cylindrical portions 50. In such an embodiment, the substrate 70 may be used as the substrate in subsequent stages of FIGS. 10A–D described below.

Figure 11:
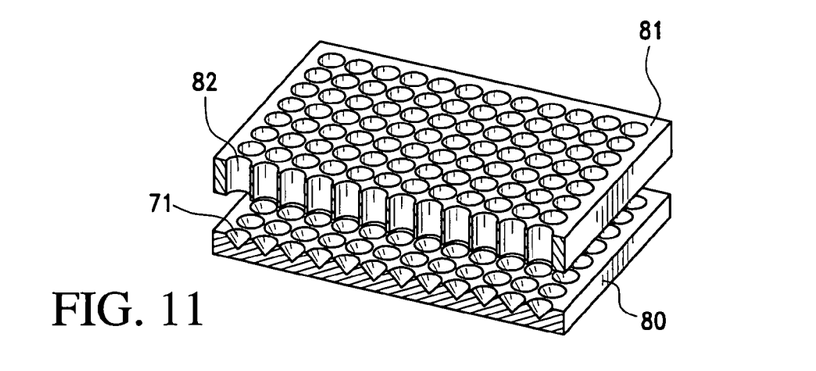
FIG. 11 depicts a method of fabricating an alternative embodiment of a cell isolation device according to the present invention.

As illustrated in FIG. 10B, in a further step of this fabrication procedure, substrate 70 is coated with a photoresist 73 and as illustrated in FIG. 10C, a mask 74 defining regions 75, the dimensions of which correspond to the dimensions of microwell portion 52, is placed over photoresist 73. Ultraviolet (UV) light is then exposed through mask 74 onto photoresist 73 and the exposed photoresist is washed with a developer solution resulting in the formation of conical-microwell master 76 as seen in FIG. 10D. Material for the cell isolation device 10a is then either spin cast, injected, or molded over conical-microwell master 76 and cured, resulting in formation of the conical-microwell member 80 as seen in FIG. 11. Photolithographic techniques are well-known to one of skill in the art and as such, substrate 70 materials, photoresist 73 materials, mask 74 materials, developer solutions, the use thereof, including variations of described technique, are well within the knowledge of one of skill in the art.

Referring to FIG. 11, in embodiments where it is desired to only have each cell isolation region 20a defined by microwell portion 52 and to only have conical portion 51 as the accessory cell delivery portion, such as the embodiment of FIG. 8B, then conical-microwell member 80 comprises the entire single cell isolation device 10a. In the alternative, in embodiments where it is desired to have accessory delivery portions, cylindrical portion 50 and conical portion 51, such as the embodiment of FIG. 8A, then a member 81 defining a plurality of cylindrical through-holes 82 may be utilized as illustrated in FIG. 11. In this embodiment, member 81 is aligned with member 80 such that when member 81 is contacted with member 80, cylindrical through-holes 82 are brought into registration with conical elements 71 to form the plurality of accessory delivery portions (cylindrical portion 50 and conical portion 51) adjoining cell isolation region (microwell portion 52).

Figure 12A:
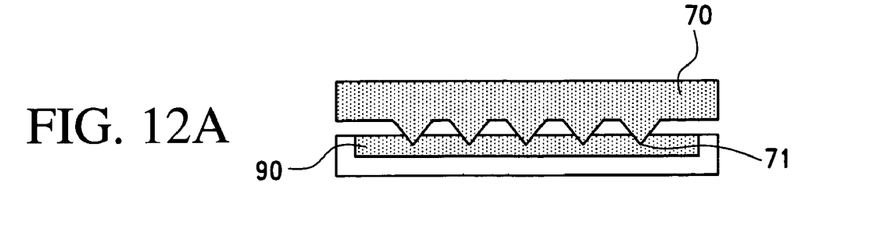
FIGS. 12A–C show respective stages of a method of fabricating an embodiment of a cell isolation device according to the present invention.
Figure 12B:
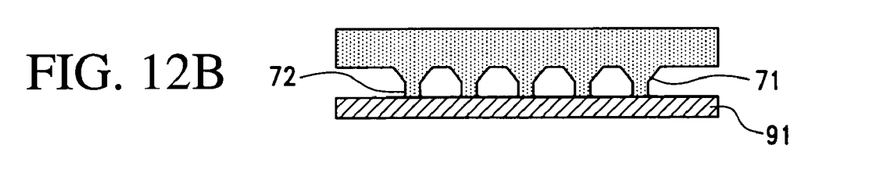
Figure 12C:
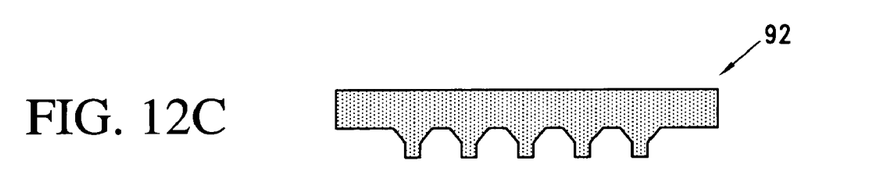

As shown in FIGS. 12A–12C, another embodiment of a method of fabricating a cell isolation device 10a having cell isolation region 20a adjoining accessory delivery portions of is through the use of surface tension driven epoxy molding. According to this embodiment, a substrate 70 similar to the one described in relation to FIGS. 10A–E may be used. Here, conical elements 71 of substrate 70 are immersed into a liquid 90 such as, for example, UV-curable epoxy as shown in FIG. 12A. Liquid drops 72 form at the tips of conical elements 71 and these liquid drops 72 are contacted with a support 91 as shown in FIG. 12B. Surface tension forces cause the liquid drops 72 to take on a known geometry, such as a cylindrical geometry. It will be recognized by one of skill in the art that the conical elements 71 should be properly aligned and oriented in relation to support 91 to assure uniformity of the liquid cylindrical shape. The liquid 72 is then cured into solid form resulting in the formation of a conical-microwell master 92 as seen in FIG. 12C. Material for the cell isolation device 10a is then either spin cast, injected, or molded over cell isolation region master 92 resulting in the formation a conical-microwell member 80 as shown by way of example in FIG. 11, and as further shown in the embodiment of FIG. 9B.

Figure 13A:
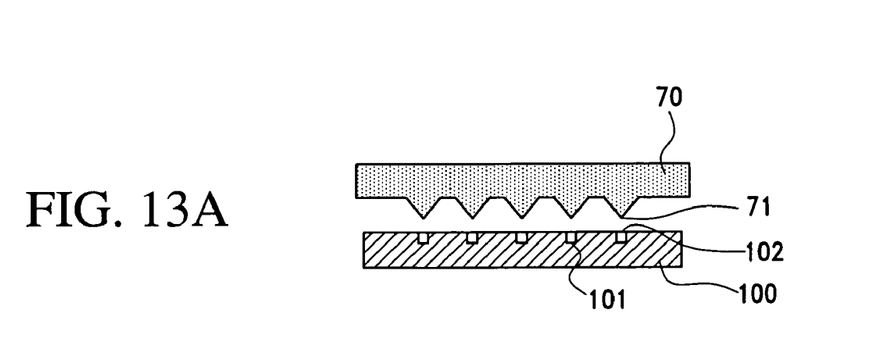
FIGS. 13A–C shows respective stages of a method of fabricating an embodiment of a cell isolation device according to the present invention.
Figure 13B:
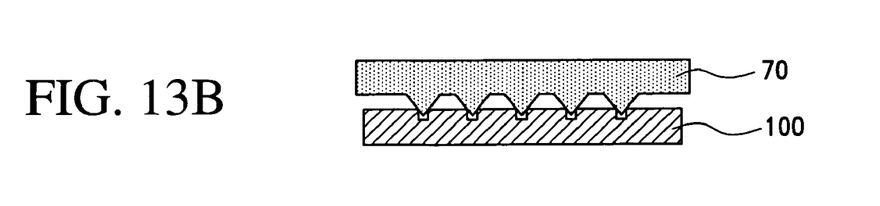
Figure 13C:
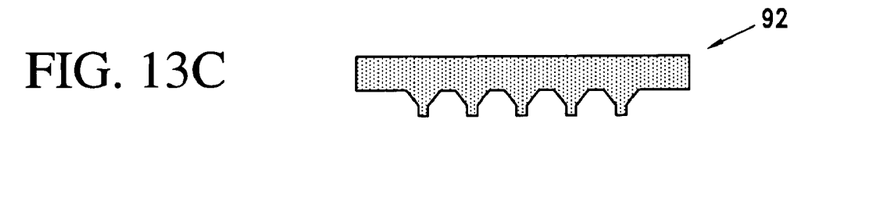

As shown in FIGS. 13A–13C, an alternative method of fabricating a cell isolation device 10a according to the present invention, is through the use of epoxy molding in microfabricated wells. This method involves the use of a substrate 70 similar to the one described in relation to FIGS. 12A–C and a microwell housing 100 as seen in FIG. 13A.

Microwell housing 100 may be fabricated of photoresist, or cast in an elastomer such as PIMS. Microwell housing 100 defines a plurality of microwell 101 therein, each of which has dimensions that correspond to the dimensions of microwell portion 52. Preferably, the microwell 101 are disposed relative to one another to match a pitch of a standard microtiter plate. Microwell 101 are filled with liquid 102, such as, for example, UV-curable epoxy. If needed, excess liquid can be removed from the areas of microwell housing 100 surrounding microwell 101 by any means known in the art such as, for example, using a "squeegee" or "doctor blade," or razor thereby leaving only liquid in microwell 101. As shown in FIG. 13B, conical elements 71 of substrate 70 and microwell 101 of microwell member 100 are aligned such that conical elements 71 are in registration with their corresponding microwell 101. Conical elements 71 are then immersed into their respective microwell 101 and the liquid inside microwell 101 is cured into a solid form. Conical elements 71 are then removed from their respective microwell 101 resulting in the formation of conical-microwell master 92 as seen in FIG. 12C. Material for the cell isolation device 10a is then either spin cast, injected, or molded over cell isolation region master 92 to form conical-microwell member 80.

Materials for cell isolations device 10a include any rigid or flexible machinable material such as glass, co-polymer or polymer, most preferably urethane, rubber, molded plastic, polymethyl methacrylate (PMMU), polycarbonate, polytetrafluoroethylene (TEFLON), polyvinyl chloride (PVC), polydimethylsiloxane (PIMS), polysulfone, and the like.

Cell isolation device 10a (whether designed to isolate a single cell or a group of cells) may be exposed to differential surface treatment in order to ensure that cells are isolated in cell isolation region 20a. For example, the areas of housing 11 surrounding cell isolation regions 20a may be treated to reduce protein adhesion while cell isolation regions 20a may be treated to provide a more hydrophilic environment. The hydrophilic nature of cell isolation region 20a versus the surrounding hydrophobic housing 11 would favor the beading of liquid containing cells 30 in cell isolation region 20a and potentially hold cells 30 in place, limiting the exhibition of biological activity, such as antibody deposition, to the "wet" areas. Examples of some hydrophobic surface treatments known in the art are teflon, perfluoronated plastic, and polyethylene glycol.

In another embodiment of the cell isolation device 10 according to the present invention, cell isolation device lob comprises a surface 40 having a plurality of cell isolation regions 20b as seen in FIG. 7 for receiving cells 30 thereon. In particular, cell isolation region 20b corresponds to a bioaffinity region upon which cells are immobilized. The ability to secure cells 30 to the bioaffinity region according to the embodiment of FIG. 7 may be accomplished through the use of bioaffinity ligands that are immobilized on the surface of the bioaffinity region and that are capable of binding to cells 30. The term "bioaffinity ligand" is defined herein to mean any biological or other organic molecule capable of specific or nonspecific binding or interaction with another biological molecule (including biological molecules on the surface of cells). Such binding or interaction may be referred to as "ligand/ligate" binding or interaction and is exemplified by, but not limited to, antibody/antigen, antibody/hapten, enzyme/substrate, enzyme/inhibitor, enzyme/cofactor, binding protein/substrate, carrier protein/substrate, lectin/carbohydrate, receptor/hormone, nucleic acid/nucleic acid, oligonucleotides/nucleic acid, receptor/effector or repressor/inducer bindings or interactions. Examples of bioaffinity ligands used herein, include but are not limited to antibodies, Self-Assembled Monolayers ("SAMs") with biospecific ligands, lectins (e.g. Ulex europaeus I lectin which binds to the terminal L-fucosyl residues present on the surface of human endothelial cell; peanut agglutinin, agglutinin-I, and phytohaem agglutinin), carbohydrates, antigens, and lipid bilayers. The bioaffinity region of cell isolation region 20b may be coated with bioaffinity ligands to either specifically or non-specifically bind the plasma membrane of cells 30.

With respect to non-specific affinity, exemplary bioaffinity ligands having a general non-specific affinity to cells are the lanthanides and in particular, erbium, which is known to bind cell surface glycoproteins as well as calcium-receptors. Another bioaffinity ligand having a general non-specific affinity to cells is ferritin.

In another embodiment, the bioaffinity ligand is an antibody specific for mammalian cells. For example, anti-Ig kappa light chain antibody, anti-CD45R antibody, or anti-syndecan, may be used to differentially bind activated B-cells. Preferably, an antibody specific for anti-Ig kappa light chain antibody cells is used. Any of the methods known in the art for conjugating an antibody to a solid phase support, such as surface 40 described herein, can be used in the present invention.

The use of SAMs provides a preferred method for binding and isolating cells 30 in the bioaffinity region of cell isolation region 20b. SAMs are the most widely studied and best developed examples of nonbiological, self-assembling systems. They form spontaneously by chemisorption and self-organization of functionalized, long-chain organic molecules onto the surfaces of appropriate substrates. SAMS are usually prepared by immersing a substrate in the solution containing a ligand that is reactive toward the surface, or by exposing the substrate to the vapor of the reactive species. As is well-known to one of skill in the art, there are many systems known in the art to produce SAMs. In certain embodiments, it may be desirable to pattern the SAMs to have an arrayed surface. Patterning SAMs on a planar surface has been achieved by a wide variety of techniques, including micro-contact printing, photo-oxidation, photo-crosslinking, photo-activation, photolithography/plating, electron beam writing, focused ion beam writing, neutral metastable atom writing, SPM lithography, micro-machining, micro-pen writing. A preferred method is micro-contact printing is described in U.S. Pat. No. 5,776,748 and is herein incorporated by reference in its entirety.

With respect to the dimensions of cell isolation region 20b according to the embodiment of FIG. 7, cell isolation regions 20b of cell delivery device 10b may be between 10 μm to 30 μm in diameter and preferably between about 10 μm to about 15 μm in diameter and may be disposed relative to one another to match a pitch of a standard microtiter plate.

As with cell isolation device 10a, cell isolation device 10b may be exposed to differential surface treatment in order to ensure that cells are isolated in cell isolation region 20b. For example, the areas of surface 40 surrounding cell isolation regions 20b may be treated, for example, with a hydrophobic surface treatment, to reduce protein adhesion. The bioaffinity region of cell isolation region 20a and the surrounding hydrophobic area of surface 40 would favor the binding of cells 30 on cell isolation region 20b. Examples of some hydrophobic surface treatments known in the art are teflon, perfluoronated plastic, and polyethylene glycol.

Although the description of the foregoing embodiments has focused on the use of bioaffinity ligands to bind cells 30 onto cell isolation region 20b of cell isolation device 10b, it is also contemplated by the present invention that bioaffinity ligands may be immobilized on the bottom surface of cell isolation regions 20a of cell isolation device 10a to potentially bind cells 30.

With respect to surface 40 of cell delivery device 10b, surface 40 may be fabricated of any material capable of having bioaffinity ligands immobilized therein and such materials are readily known to one of skill in the art. Preferably, surface 40 is fabricated of any rigid or flexible machinable material such as glass, co-polymer or polymer, most preferably urethanes, rubber, molded plastic, polymethylmethacrylate (PMMA), polycarbonate, polytetrafluoroethylene (TEFLONTM), polyvinylchloride (PVC), polydimethylsiloxane (PDMS), polysulfone, and the like. Such substrates are readily manufactured from microfabricated masters, using well known molding techniques, such as injection molding, embossing or stamping, or by polymerizing the polymeric precursor material within a mold. Standard soft lithography techniques may also be used to fabricate surface 40 (see e.g., Love, et al., MRS BULLETIN, pp. 523–527 (July 2001) "Fabrication of Three-Dimensional Microfluidic Systems by Soft Lithography," Delamarche et al,: JOURNAL OF AMERICAN CHEMICAL SOCIETY, Vol. 120, pp. 500–508 (1998), Delamarche et al,: SCIENCE, Vol. 276, pp. 779–781 (May 1997), Quake et al., SCIENCE, Vol. 290, pp. 1536–1540 (Nov. 24, 2000), U.S. Pat. No. 6,090,251, all of which are hereby incorporated by reference). Such surface materials are preferred for their ease of manufacture, low cost and disposability, as well as their general inertness to most extreme reaction conditions. These materials may include treated surfaces, such as, derivatized or coated surfaces, to enhance their utility in the fluidic, preferably microfluidic, system, to provide enhanced fluid direction (See e.g., U.S. Pat. No. 6,238,538, and which is incorporated herein by reference).

Figure 14:
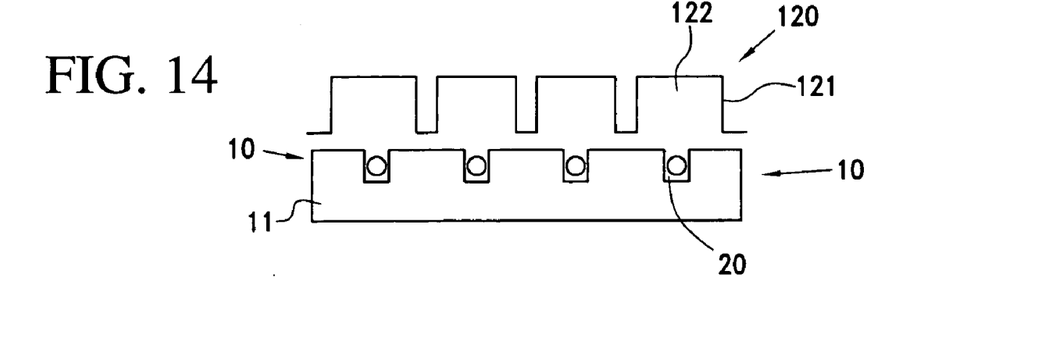
FIG. 14 is a cross-sectional view of an embodiment of a cell expansion device according to the present invention.
Figure 15A:
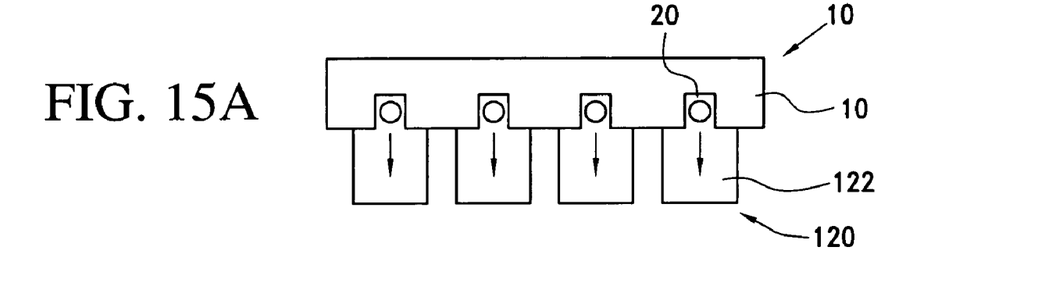
FIG. 15A shows a method of transferring cells from the cell isolation device to an embodiment of the cell expansion device according to the present invention.

Once cells 30 are isolated in cell isolation regions 20 of cell isolation device 10, another aspect of the invention allows for the proliferation of the cells 30 through the use of a cell expansion device. As illustrated in FIG. 14, the cell expansion device 120 comprises a structure 121 defining a plurality of wells 122 with adjacent wells having the same pitch as the pitch defined by adjacent cell isolation regions of the cell isolation device 10. In particular, each well 122 in a test orientation of the cell expansion device 120, encompasses a cavity surrounded by two lateral sides connected to a bottom side. Preferably, each well is also characterized by having a greater volume than respective ones of the cell isolation region 20. "Wells" as used herein are specific to the cell expansion device, whereas cell isolation regions as used herein are specific to the cell isolation device. In general as seen in FIG. 14, cell expansion device 120 is utilized by orienting structure 121 with housing 11 of cell isolation device 10 such that wells 122 overlie corresponding ones of the cell isolation regions 20. Structure 121 is then placed in direct contact with housing 11 to form a seal such that fluid communication between cells 30 in adjacent cell isolation regions is inhibited. As seen in FIG. 15A, the mated cell isolation device/cell expansion device is then inverted and cells 30 are transferred, for example by centrifugal force, from cell isolation regions 20 to wells 122.

Figure 15B:
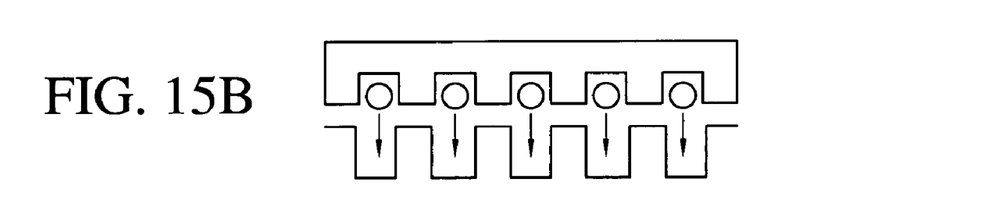
FIG. 15B shows a method of transferring cells from the cell isolation device to an alternative embodiment of the cell expansion device according to the present invention.
Figure 16:
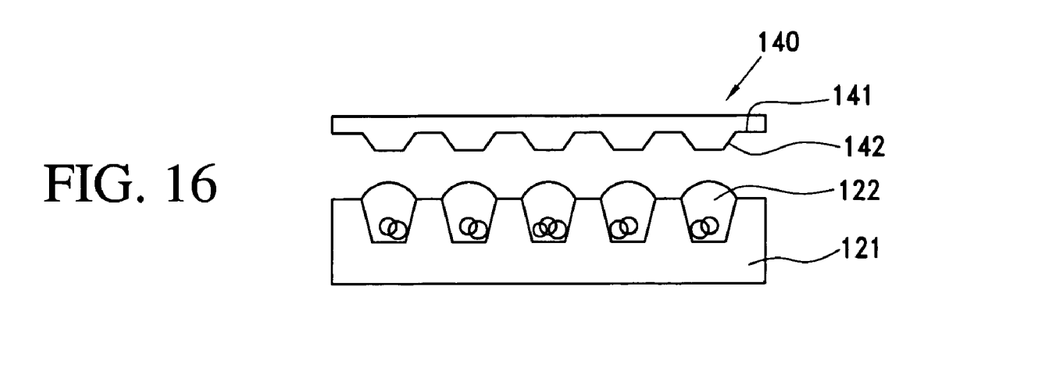
FIG. 16 depicts a cross-sectional view of an embodiment of the detection device and a method of detecting antibody production according to the present invention.

Wells 122 may be of any shape, but wells with circular or square shaped top plan view (or transverse cross-sections) are preferred as these shapes are commonly used in the industry. Nothwithstanding the shape, wells 122 of expansion device 120 preferably have a greater volume than cell isolation regions 20 such as, for example, having a greater diameter (as illustrated in FIG. 15A) or a greater depth (as illustrated in FIG. 15B). Preferably wells 122 have the same diameter as cell isolation regions 20 of cell delivery device 10. More preferably, the wells 122 of the expansion device 120 have a depth of about 2 mm. In one embodiment, the lateral surfaces of well 122 are canted relative to one another or to the bottom surface of the well 122 in a test orientation of cell expansion device 120 as shown in FIG. 16. Canted wells 122 permit easier access by allowing for lateral movement when performing downstream experiments on cells 30 in wells 122 and may create a more uniform interface with a small cell isolation region 20. On the other hand, a well 122 that has lateral sides that are at a 90° angle to the bottom side of the well 122 in a test orientation of the cell expansion device 120 provide a greater volume, which may increase the time available for the detection step to be described below.

Structure 121 is intended to define any number of wells 122, but preferably defines the number of wells in a standard microtiter plate such as a 24-, 96-, 384-, 768-, or 1536-well plate. More preferably, structure 121 defines the number of wells of a 385-well plate or 1536-well plate. Approximately 2 μl of liquid can be held per well 122 in a standard 1536 well plate. Larger well volumes can be achieved by extending the depth of the well 122 without compromising the correspondence between the pitch between adjacent wells 122 and the pitch between adjacent cell isolation regions 20.

Figure 17:
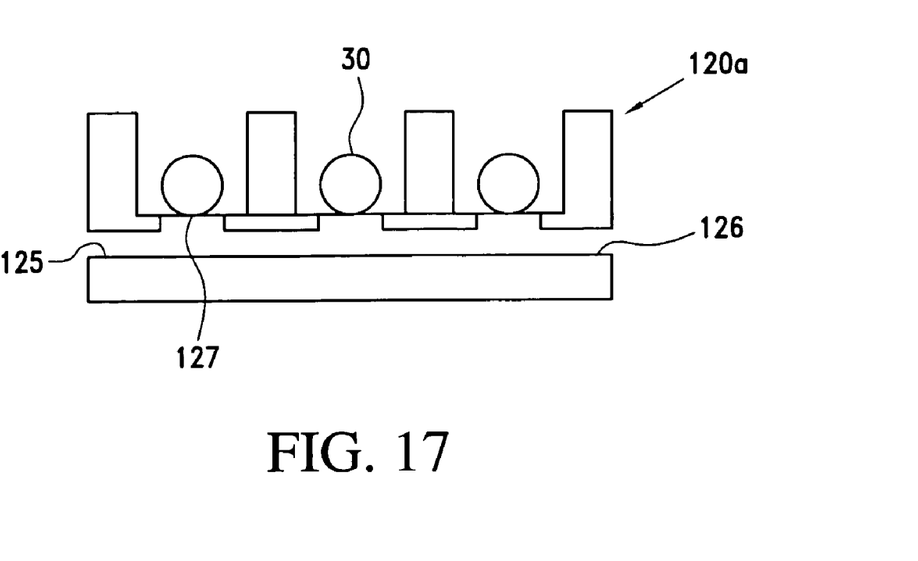
FIG. 17 is a cross-section view of an alternative embodiment of a cell expansion device according to the present invention.

In another embodiment of cell expansion device 120 as seen in FIG. 17, cell expansion device 120a is configured such that the respective wells 122a are accessible from a bottom side 127 thereof in a test orientation of cell expansion device 120a. Structure 123a further defines an entrance port 125 and optionally, an exit port 126. The wells' 122a accessibility from the bottom side 127 permits exchange of media, thereby facilitating cell expansion and refeeding. Cells 30 are retained from passing through the access to the bottom side 127 of well 122a by a block such as a size constraint or semi-permeable membrane, such as a dialysis membrane, nitrocellulose or perforated polydimethylsialoxane, for example. The semi-permeable membrane of this embodiment also allows for gas exchange while reducing the evaporation of liquid contained in each well 122a. The initial flow-through of old medium may be drained by positive pressure, vacuum, or gravity to capture liquid potentially containing antibody or another product of the desired biological activity, on a surface designed for sampling/detection, e.g., nitrocellulose, glass, urethanes, rubber, molded plastic, or polydimethylsialoxane.

Preferably, the material used for the manufacture of cell expansion device 120 comprises any rigid or flexible material such as glass, urethanes, rubber, molded plastic, co-polymer or polymer, more preferably urethanes, rubber, molded plastic, polymethylmethacrylate (PMMA), polycarbonate, polytetrafluoroethylene (TEFLON™), polyvinylchloride (PVC), polydimethylsiloxane (PDMS), polysulfone, and the like, and most preferably PDMS. Such materials are readily manufactured from fabricated masters, using well known molding techniques, such as injection molding, embossing or stamping, or by polymerizing the polymeric precursor material within the mold. Such materials are preferred for their ease of manufacture, low cost and disposability, as well as their general inertness to most extreme reaction conditions.

Once the cells 30 are transferred from cell isolation device 10 to cell expansion device 122, the cells 30 are incubated in the cell expansion device 122, for a sufficient amount of time to allow for proliferation of cells 30. Cell expansion device 122 is intended to be used at any biologically viable temperature. Lowering the incubation temperature of the cells (i.e., from 37° C. to 18° C.) may, however, slow the metabolic processes of the cells 30 and reduce cell cloning time, thus extending the time for assay. Alternatively, media that is optimal for exhibiting the desired biological activity that is to be screened but not optimal for cell proliferation could also be used to extend the time for assay.

As illustrated in FIG. 16, after sufficient time has been allowed for cells 30 to grow and divide, a detection device 140 is utilized to detect the desired biological activity exhibited by the cells, such as antibody production. In the case of detecting antibody production, in one embodiment as illustrated in FIG. 16, detection device 140 generally comprises a surface 141 defining an array of prongs 142 upon which antigens are immobilized. In a preferred embodiment, surface 141 is a substantially planar surface. In one embodiment, prongs 142 are coated with the specific antigen(s) used to immunize animals from which the cells being tested are derived. In use, detection device 140 is placed over structure 121 of cell expansion device 120 such that prongs 142 are in registration with wells 122. Prongs 142 are then immersed into wells 122 of cell expansion device 120 in order to allow antigens immobilized on prongs 142 to potentially bind to antibodies secreted/produced by cells, such as hybridoma cells in wells 120. Prongs 142 of detection device 140 are then removed from well 122 of cell expansion device 120 and then immersed into a solution of detectable secondary antibody. Secondary antibodies may be visualized by standard techniques known in the art such as by enzymatic color reactions or fluorescence. A prong surface may also be interfaced with mass spectrometer for additional assay flexibility. Other methods of labeling and detecting the antibodies are well within the knowledge of one of skill in the art and therefore are not discussed in detail herein.

The antibodies may be coated on prongs 142 through non-specific physisorption or through the use of SAMs on prongs 142. For example, a particular antigen may be specifically patterned on prong 142 by first evaporating gold on a polyurethane prong, then adding a self-assembling monolayer onto which an antigen can be covalently linked. (See, e.g., Mrksich et al., Annu. Rev. Biophys. Biomol. Struct., vol. 25 (1996) incorporated herein by reference). Additionally, other strategies for immobilizing protein may be employed such as lysine linkage, cutinase linkage, GST-fusion or GPI linkage.

Figure 18:
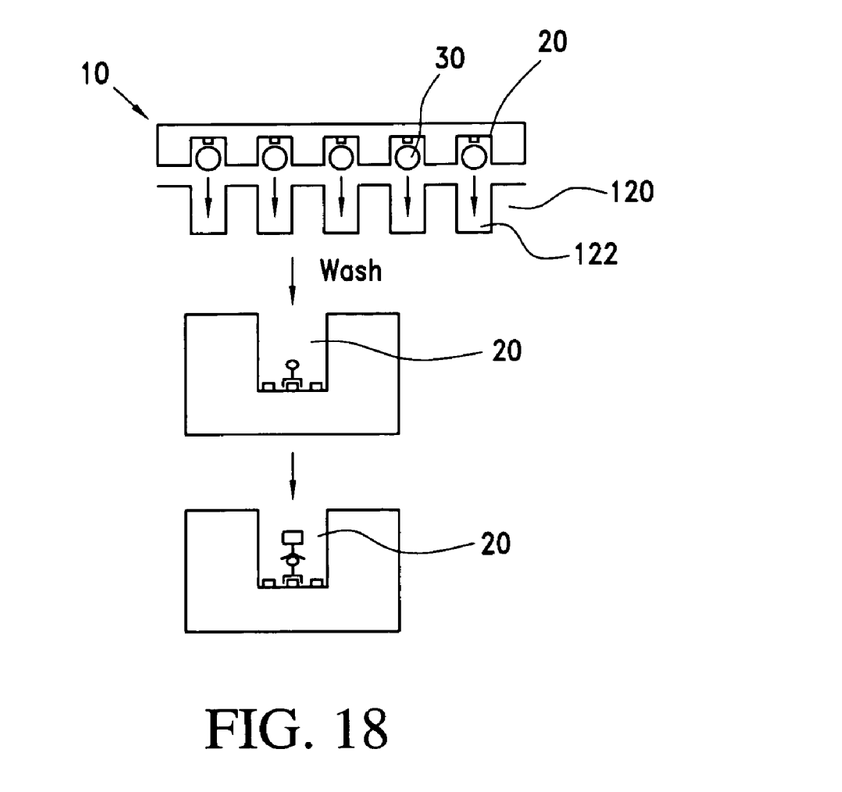
FIG. 18 shows a method of detecting antibody production according to the present invention.

In another embodiment of a detection device used to detect the production of antibodies from cells, such as, for example, hybridoma cells, cell isolation device 10 additionally serves as a detection device as shown in FIG. 18. In this embodiment, the bottoms of cell isolation regions 20 of cell isolation device 10 are coated with the specific antigen(s) used to immunize animals from which the hybridomas being tested are derived. If the desired biological activity being screened is the production of a biological product, other than antibodies, the bottoms of cell isolation regions 20 could be coated with a ligand that binds to the biological product (ligate) produced by the desired biological activity that is being screened. Ligands include, for example, a peptide, hormone, enzyme, or carbohydrate. Cells 30 are then delivered to cell isolation regions 20 and the cells 30 will begin to produce antibodies that will bind the antigens coated on cell isolation regions 20. Cells 30 are then transferred from the cell isolation regions 20 of cell isolation device 10 to the wells 122 of cell expansion device 120. The antibodies bound to the antigens on the bottoms of cell isolation regions 20 are then detected using an ELISA sandwich or a variety of detection methods known in the art such as secondary antibody coupled to alkaline phosphatase, horse radish peroxidase, etc.

Although in the embodiment illustrated in FIG. 16, cell isolation region 20 of the cell isolation device 10 actually becomes the detection device, it is well within the scope of the present invention to utilize a separate detection device. In such an embodiment, the detection device comprises a structure defining a plurality of indentations sized to receive cells from cell expansion device 120, wherein the bottom of the indentations are coated with a ligand that binds to the biological product (ligate) produced by the desired biological activity that is being screened. Such ligates include, for example, a protein, enzyme, peptide, carbohydrate or antibody. After cells are transferred from cell isolation device 10 to the cell expansion device 120, cells are, in turn, transferred to the indentations of the cell detection device where they will potentially express the biological product of the desired biological activity that is being screened and such biological product binds its complementary binding pair member coated on the indentations.

Although the foregoing description of detection methods have been described in reference to production of a biological product produced by the desired biological activity being screened, the present invention contemplates the detection of any biological activity by any types of cells. Such detection methods are well known to one of skill in the art.

It will be appreciated that the present disclosure is intended to set forth the exemplifications of the invention, and the exemplifications set forth are not intended to limit the invention to the specific embodiments illustrated. The disclosure is intended to cover, by the appended claims, all such modifications as fall within the spirit and scope of the claims.

We claim:

1. A method of screening cells for a desired biological activity comprising:
    providing a cell isolation device defining a plurality of cell isolation regions, each cell isolation region being sized for isolating about one to about five cells on a surface of said cell isolation region, each cell isolation region encompassing a bioaffinity region on said surface, the cell isolation regions positioned to have a predetermined pitch with respect to one another;
    delivering the about one cell to about five cells to each of the cell isolation regions through a microfluidic channel;
    providing a cell expansion device defining a plurality of wells wherein the position of the wells of the cell expansion device corresponds to the predetermined pitch of the cell isolation regions;
    placing said cell isolation device in direct contact with said cell expansion device to form a seal such that fluid communication between cells in adjacent cell isolation regions is inhibited, inverting said cell isolation device, and transferring the about one to about five cells from said surface of said cell isolation regions to the wells;
    allowing about one cell to about five cells to proliferate and exhibit a desired biological activity; and
    assaying the biological activity of the about one to about five cells.

2. The method of claim 1, wherein the microfluidic channel has a diameter of about 100 microns.

3. The method of claim 1, wherein each of the bioaffinity regions comprises bioaffinity ligands immobilized therein.

4. The method of claim 3, wherein the bioaffinity ligands are selected from the group consisting of antibodies, antigens, self-assembled monolayers (SAMs), lectins, carbohydrates, transmembrane proteins, and transmembrane protein receptors.

5. The method of claim 1, wherein the predetermined pitch of the cell isolation regions matches a pitch of a standard microtiter plate.

6. The method of claim 1, wherein each of the cell isolation regions has a diameter of about 10 to about 30 microns.

7. The method of claim 1, wherein transferring comprises transferring about one cell to about five cells from the cell isolation device to the cell expansion device by centrifugal force.

8. The method of claim 1, wherein the cells are hybridoma cells and the biological activity exhibited by the cells is antibody production.

9. The method of claim 1, wherein assaying comprises assaying hybridoma cells for specific antibody production by:
providing a detection device comprising a member defining a plurality of prongs, the prongs coated with specific antigens;
immersing the prongs into the wells to allow potential binding between specific antibodies produced by the hybridoma cells and the antigens;
removing the prongs from the wells;
immersing the prongs into a detection solution;
detecting the presence of specific antibodies.

10. A kit for screening cells for a desired biological activity, the kit comprising:
a cell isolation device defining a plurality of cell isolation regions, each of the cell isolation regions being sized to isolate about one cell to about five cells therein, and each encompassing a bioaffinity region, the cell isolation device further defining a predetermined pitch with respect to one another;
a microfluidic device; and
a cell expansion device defining a plurality of wells wherein the wells of the cell expansion device correspond to respective regions of the cell isolation device such that the structure of said cell isolation device when placed in direct contact with said cell expansion device creates a seal that inhibits fluid communication between cells in adjacent cell isolation regions.

11. The kit of claim 10, further comprising a detection device for screening the about one to about five cells for the desired biological activity.

12. The kit of claim 10, wherein the bioaffinity regions comprise bioaffinity ligands immobilized therein.

13. The kit of claim 12, wherein the bioaffinity ligands are selected from the group consisting of antibodies, antigens, self-assembled monolayers (SAMs), lectins, carbohydrates, transmembrane proteins, and protein receptors.

14. The kit of claim 10, wherein the surface of the cell isolation device has a substantially planar surface and wherein the bioaffinity regions comprise respective discrete areas of the substantially planar surface.

15. The kit of claim 10, wherein each of the cell isolation regions has a diameter of about 10 microns to about 30 microns in diameter.

16. The kit of claim 10, wherein the cell expansion device comprises a plurality of wells comprising lateral sides canted relative to one another.

17. The device of claim 10, wherein the predetermined pitch of the cell isolation regions matches a pitch of a standard microtiter plate.

* * * * *

UNITED STATES PATENT AND TRADEMARK OFFICE
CERTIFICATE OF CORRECTION

PATENT NO. : 7,169,578 B2
APPLICATION NO. : 10/206341
DATED : January 30, 2007
INVENTOR(S) : Wang et al.

It is certified that error appears in the above-identified patent and that said Letters Patent is hereby corrected as shown below:

On the Title Page:
Item [57], line 9, "group of cell(s)." should be changed to --group of cells.--;

Title Page 2, Item [56] column 2, "Hodneland et al., "Selective immobilization of proteins to self-assembled manolayers presenting active site-directed capture ligands", PNAS. 99(8):5048-5052 (2002)." should be changed to --Hodneland et al., "Selective immobilization of proteins to self-assembled monolayers presenting active site-directed capture ligands", PNAS. 99(8):5048-5052 (2002).--;

In the Drawings:
In Figure 9A, "d2" should be changed to --d3--;
In Figure 10C, "73" should be changed to --75-- to be consistent with the description in the specification--;
In Figure 15A, the reference numeral "10" without an arrow should be changed to --11-- to be consistent with the description in the specification; and
In Figure 17, "122a" should be added to point to the respective wells and "123a" should be added to point to the structure, as described in the specification at column 12.

Column 1, line 8, "U.S. application" should be changed to --U.S. Application--;
Column 1, line 11, "Applicaton" should be changed to --Application--;
Column 1, line 12, "which herein" should be changed to --which are herein--;
Column 2, line 31, "allowing about" should be changed to --allowing the about--;
Column 2, line 33, "activity the" should be changed to --activity of the--;
Column 3, line 61, "epothelial cells" should be changed to --epithelial cells--;
Column 5, line 4, "Cell are" should be changed to --Cells are--;
Column 5, lines 30-31, "about hundred cells" should be changed to --about one hundred cells--;
Column 5, line 35, "to delivery about" should be changed to --to deliver about--;
Column 5, line 37, "to delivery about" should be changed to --to deliver about--;
Column 5, lines 39-40, "to delivery about" should be changed to --to deliver about--;

Signed and Sealed this
Fifth Day of June, 2012

David J. Kappos
*Director of the United States Patent and Trademark Office*

CERTIFICATE OF CORRECTION (continued)
U.S. Pat. No. 7,169,578 B2

Column 6, line 11, "about hundred cells" should be changed to --about one hundred cells--;
Column 6, lines 36-37, "about hundred cells" should be changed to --about one hundred cells--;
Column 6, lines 49-50, "predetermine pitch" should be changed to --predetermined pitch--;
Column 7, line 39, "defined a microwell" should be changed to --defined as microwell--;
Column 7, line 40, "portions such as" should be changed to --portion such as--;
Column 7, line 50, "corresponds to" should be changed to --correspond to--;
Column 8, line 38, "region(microwell portion 52)" should be changed to --region (microwell portion 52)--;
Column 8, lines 42-43, "portions of is through" should be changed to --portions is through--;
Column 8, line 55, "liquid 72 is" should be changed to --liquid drops 72 are--;
Column 9, line 2, "PIMS" should be changed to --PDMS--;
Column 9, line 3, "microwell 101" should be changed to --microwells 101--;
Column 9, line 5, "microwell 101" should be changed to --microwells 101--;
Column 9, line 7, "microwell 101" should be changed to --microwells 101--;
Column 9, line 10, "microwell 101" should be changed to --microwells 101--;
Column 9, line 14, "microwell 101" should be changed to --microwells 101--;
Column 9, lines 14-15, "microwell member 100" should be changed to --microwell housing 100--;
Column 9, line 16, "microwell 101" should be changed to --microwells 101--;
Column 9, lines 17-18, both instances of "microwell 101" should be changed to --microwells 101--;
Column 9, line 20, "microwell 101" should be changed to --microwells 101--;
Column 9, line 25, "cell isolations device" should be changed to --cell isolation device--;
Column 9, line 28, "polymethyl methacrylate (PMMU)" should be changed to --polymethylmethacrylate (PMMA)--;
Column 9, lines 28-29, "polytetrafluoroethylene (TEFLON)" should be changed to --polytetrafluoroethylene (TEFLON®)--;
Column 9, line 30, "polydimethylsiloxane (PIMS)" should be changed to --polydimethylsiloxane (PDMS)--;
Column 9, line 44, "teflon" should be changed to --TEFLON®--;
Column 10, line 32, "SAMS" should be changed to --SAMs--;
Column 10, line 46, "printing is described" should be changed to --printing as described--;
Column 10, line 63, "teflon" should be changed to --TEFLON®--;
Column 11, lines 12-13, "polytetrafluoroethylene (TEFLONTM)" should be changed to --polytetrafluoroethylene (TEFLON®)--;
Column 11, line 34, "6,238,538 and which is" should be changed to --6,238,538 which is--;
Column 12, line 22, "385-well plate" should be changed to --384-well plate--;
Column 12, lines 39-40, "polydimethylsialoxane" should be changed to --polydimethylsiloxane--;
Column 12, line 48, "polydimethylsialoxane" should be changed to --polydimethylsiloxane--; and
Column 14, line 2, "horse radish" should be changed to --horseradish--